US008481465B2

(12) United States Patent
Elomari et al.

(10) Patent No.: US 8,481,465 B2
(45) Date of Patent: *Jul. 9, 2013

(54) SYNTHESIS OF BIOLUBRICANT ESTERS FROM UNSATURATED FATTY ACID DERIVATIVES

(75) Inventors: Saleh A. Elomari, Fairfield, CA (US); Stephen Joseph Miller, San Francisco, CA (US); Zhen Zhou, Emeryville, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/553,611

(22) Filed: Jul. 19, 2012

(65) Prior Publication Data

US 2012/0283160 A1    Nov. 8, 2012

Related U.S. Application Data

(62) Division of application No. 12/498,663, filed on Jul. 7, 2009, now abandoned.

(51) Int. Cl.
C10M 105/36 (2006.01)
C10M 105/38 (2006.01)
C07C 67/00 (2006.01)
C07C 69/00 (2006.01)

(52) U.S. Cl.
USPC ............ 508/485; 508/459; 508/506; 560/263

(58) Field of Classification Search
USPC .................. 560/263; 508/450, 485, 506, 496
See application file for complete search history.

(56) References Cited

U.S. PATENT DOCUMENTS

| 7,871,967 B2 * | 1/2011 | Miller et al. .................. 508/459 |
| 2006/0019840 A1 * | 1/2006 | Kawahara et al. ............ 508/280 |
| 2008/0194444 A1 * | 8/2008 | Miller et al. .................. 508/496 |

* cited by examiner

*Primary Examiner* — Pamela H Weiss
(74) *Attorney, Agent, or Firm* — Jeffrey McQuiston; Penny Prater; Susan M. Abernathy

(57) ABSTRACT

The present invention is generally directed to diester-based lubricant compositions comprising one or more isomeric mixtures of diester species. The present invention is also directed to methods of making these and other similar lubricant compositions. In some embodiments, the methods for making such diester-based lubricants utilize a biomass precursor material from which mono-unsaturated free lipid species can be provided or otherwise generated, wherein such mono-unsaturated free lipid species are converted to isomeric diol species en route to the synthesis of diester species for use as/in the diester-based lubricant compositions.

12 Claims, 6 Drawing Sheets

Table 1.

| Viscosity @ 40°C | 18.4 mm$^2$/s |
|---|---|
| Viscosity @ 100°C | 4.5 mm$^2$/s |
| Viscosity Index | 168 |
| Cloud Point | 6°C |
| Pour Point | 3°C |
| Oxidation Stability | 26.9 hr/L |

*Fig. 6*

SYNTHESIS OF BIOLUBRICANT ESTERS FROM UNSATURATED FATTY ACID DERIVATIVES

CROSS REFERENCE TO RELATED APPLICATIONS

This application is a divisional application of co-pending application Ser. No. 12/498,663, filed Jul. 7, 2009 and claims priority therefrom.

FIELD OF THE INVENTION

This invention relates to ester-based lubricants and specifically to diester-based lubricants and their manufacture—particularly wherein they are made from at least one biologically-derived precursor.

BACKGROUND

Esters have been used as lubricating oils for over 50 years. They are used in a variety of applications ranging from jet engines to refrigeration. In fact, esters were the first synthetic crankcase motor oils in automotive applications. However, esters gave way to polyalphaolefins (PAOs) due to the lower cost of PAOs and their formulation similarities to mineral oils. In full synthetic motor oils, however, esters are almost always used in combination with PAOs to balance the effect on seals, additives solubility, volatility reduction, and energy efficiency improvement by enhanced lubricity.

Ester-based lubricants, in general, have excellent lubrication properties due to the polarity of the ester molecules of which they are comprised. The polar ester groups of such molecules adhere to positively-charged metal surfaces creating protective films which slow down the wear and tear of the metal surfaces. Such lubricants are less volatile than the traditional lubricants and tend to have much higher flash points and much lower vapor pressures. Ester-based lubricants are excellent solvents and dispersants, and can readily solvate and disperse the degradation by-products of oils. Therefore, they greatly reduce sludge buildup. While ester-based lubricants are stable to thermal and oxidative processes, the ester functionalities give microbes a handle to do their biodegrading more efficiently and more effectively than their mineral oil-based analogues. However, the preparation of esters is more involved and more costly than the preparation of their PAO counterparts.

Diester-based lubricants and their manufacture have been recently reported, wherein the diester species have a general formula:

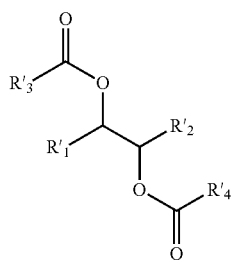

where $R'_1$, $R'_2$, $R'_3$, and $R'_4$ are the same or independently selected from a $C_2$ to $C_{17}$ carbon fragment. See commonly-assigned U.S. patent application Ser. Nos. 11/673,879 (Miller et al.), filed Feb. 12, 2007 and published as United States Patent Publication No. US 20080194444 on Aug. 14, 2008; and Ser. No. 12/023,695 (Miller et al.), filed Jan. 31, 2008. Note that the two ester groups are vicinal in their attachment to the aliphatic backbone of the diester species.

In view of the foregoing, and not withstanding such above-described advances in diester-based lubricant synthesis, facile methods of generating diester-based lubricants would be extremely useful—particularly wherein the diester species in said lubricants can deviate from the vicinal arrangement of the esters groups in relation to their aliphatic backbone.

BRIEF DESCRIPTION OF THE INVENTION

The present invention is generally directed to diester-based lubricant compositions, such compositions generally comprising one or more isomeric mixtures of diester species. The present invention is also directed to methods of making these and other similar lubricant compositions. In some embodiments, the methods for making such diester-based lubricants make at least partial use of one or more biomass precursor species as reagents in the synthesis of such diester species. Indeed, in some embodiments such diester-based lubricants can be entirely bio-derived. In some or other embodiments, lubricant precursor species can also be sourced or otherwise derived from Fischer-Tropsch (FT) reaction products/byproducts.

In some embodiments, the present invention is directed to at least one lubricant composition comprising a quantity of at least one isomeric mixture of diester species, the diester species (1a) and (1b) having the following structures:

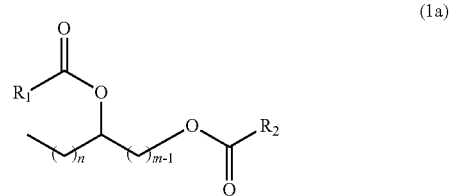

(1a)

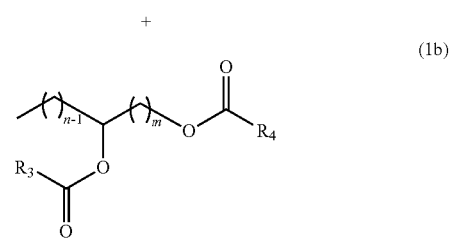

(1b)

wherein $R_1$, $R_2$, $R_3$, and $R_4$ are the same or independently selected from $C_2$ to $C_{20}$ hydrocarbon groups, and wherein "n" and "m" are integers from 2 to 20. In some such compositional embodiments, the isomeric diester species, of which the at least one isomeric mixture is comprised, have a molecular mass that is from at least about 400 atomic mass units (a.m.u.) to at most about 1100 a.m.u., and more typically between 450 a.m.u. and 1000 a.m.u.

In terms of physical and lubricative properties, in some embodiments the kinematic viscosity of the above-described composition at a temperature of 100° C. is at least 3 mm²/s, i.e., 3 centistokes (cSt). In some or other embodiments, said composition has a pour point of less than −20° C. Typically, such properties are such that, in at least some embodiments, the compositions can be used as lubricants in one or more of a variety of applications and environments.

In some embodiments, the above-described composition comprises quantities of at least two different isomeric mixtures of diester species—typically with large variability in relative amounts. In some or other embodiments, said composition further comprises a base oil selected from the group consisting of Group I oils, Group II oils, Group III oils, and combinations thereof. Additionally or alternatively, in some embodiments, said composition further comprises one or more monoester and/or triester species.

In some embodiments, the present invention is directed to methods of making the above-described composition(s), such methods comprising the steps of: (A) converting a quantity of mono-unsaturated free lipid species (e.g., mono-unsaturated fatty acid(s) and/or ester(s)), having a carbon number of from 10 to 22, to an isomeric mixture of diol species having the same carbon number as the free lipid species from which they were derived, wherein said converting proceeds via an epoxide intermediate species; and (B) esterifying the isomeric mixture of diol species with an esterifying species to form an isomeric mixture of diester species, wherein the isomeric mixture of diester species comprises isomerically-related structures 1a and 1b, and wherein $R_1$, $R_2$, $R_3$, and $R_4$ are the same or independently selected from $C_2$ to $C_{20}$ hydrocarbon groups, and wherein n and m are the same or independently selected from the group of integers 2 to 20.

In some such above-described method embodiments, the step of converting comprises the following sub-steps: (Substep A) epoxidizing the quantity of mono-unsaturated free lipid species to yield a quantity of epoxidized lipid species; and (Substep B) reducing the epoxidized lipid species to yield an isomeric mixture of diol species—which is subsequently esterified to yield an isomeric mixture of diester species.

In some embodiments, variations on the above-described method embodiments are found wherein the step of converting comprises the following alternate (variational) substeps: (Alt. Substep A) reducing the quantity of mono-unsaturated free lipid species to yield a quantity of mono-unsaturated fatty alcohol species; (Alt. Substep B) epoxidizing the quantity of mono-unsaturated fatty alcohol species to yield a quantity of epoxidized alcohol species; and (Alt. Substep C) reducing the epoxidized alcohol species to yield an isomeric mixture of diol species.

The foregoing has outlined rather broadly the features of the present invention in order that the detailed description of the invention that follows may be better understood. Additional features and advantages of the invention will be described hereinafter which form the subject of the claims of the invention.

BRIEF DESCRIPTION OF THE DRAWINGS

For a more complete understanding of the present invention, and the advantages thereof, reference is now made to the following descriptions taken in conjunction with the accompanying drawings, in which:

FIG. 6 (Table 1) lists lubrication and physical properties of isomeric diester mixture 4a/4b, as prepared in Example 4.

DETAILED DESCRIPTION OF THE INVENTION

1. Introduction

Figure 1:
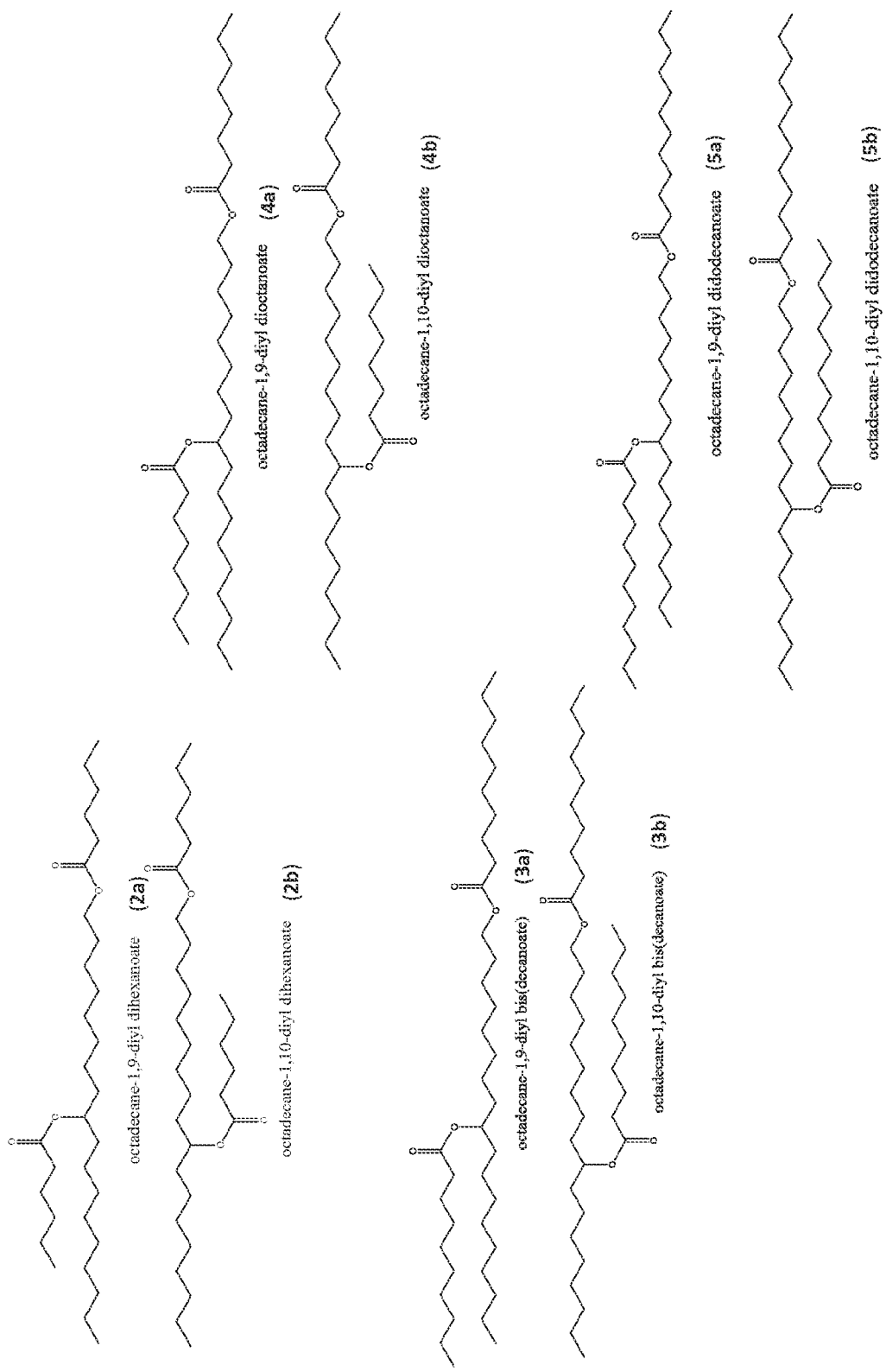
FIG. 1 depicts four exemplary isomeric diester pairs 2a-5a and 2b-5b, suitable for use as lubricants and/or lubricant components, in accordance with some embodiments of the present invention.

The present invention is generally directed to diester-based lubricant compositions comprising isomeric mixtures of diester species. The present invention is also directed to methods (processes) of making these and other similar lubricant compositions. In many of these embodiments, the methods for making such diester-based lubricants utilize one or more biomass precursor species, wherein it is typically at least the lipid components utilized in such methods that are obtained from biomass sources (e.g., vegetable oil and/or algae). Other chemical components used in such methods can be similarly derived from biomass, or they can be derived from other sources such as, but not limited to, Fischer-Tropsch (FT) synthesis products and/or by-products.

Because biolubricants and biofuels are increasingly gaining ground and becoming topics of focus for many in the oil/petroleum industry, the use of biomass in the making of such above-mentioned lubricants could be attractive from several different perspectives. To the extent that biomass is so utilized in making the diester-based lubricants of the present invention, such lubricants are deemed to be biolubricants.

An advantage of the diester lubricants described herein, in at least some embodiments, is that they can be entirely bio-derived; i.e., all of the reagents used in their synthesis (generally exclusive of solvents and catalysts) can be derived from a biological precursor material. Additionally, methods for producing such lubricants make use of olefins already present in vegetable/crop oils, thereby streamlining the synthetic process. Additionally still, as opposed to conventional biolubricants, i.e., triglycerides, the diester-based lubricants described herein have, in at least some embodiments, excellent low temperature properties without having carbon-carbon double bonds, the presence of such bonds generally compromising the lubricant composition's oxidation stability.

2. Definitions

"Lubricants," as defined herein, are substances (usually a fluid under operating conditions) introduced between two moving surfaces so to reduce the friction and wear between them. Base oils used as motor oils are generally classified by the American Petroleum Institute as being mineral oils (Group I, II, and III) or synthetic oils (Group IV and V). See American Petroleum Institute (API) Publication Number 1509.

"Pour point," as defined herein, represents the lowest temperature at which a fluid will pour or flow. See, e.g., ASTM Standard Test Method D 5950-02 (R 2007).

"Cloud point," as defined herein, represents the temperature at which a fluid begins to phase separate due to crystal formation. See, e.g., ASTM Standard Test Method D 5771-05.

"Centistoke," abbreviated "cSt," is a unit for kinematic viscosity of a fluid (e.g., a lubricant), wherein 1 centistoke equals 1 millimeter squared per second (1 cSt=1 mm²/s). See, e.g., ASTM Standard Guide and Test Method D 2270-04.

"Oxidation stability," as defined herein, generally refers to a composition's resistance to oxidation. Oxidator BN is a convenient way to measure the oxidation stability of base oils, and it is the method used to evaluate the oxidation stability of at least some of the lubricant compositions described herein. The Oxidator BN test is described by Stangeland et al. in U.S. Pat. No. 3,852,207, which issued on Dec. 3, 1974. The Oxidator BN test measures an oil's resistance to oxidation by means of a Dornte-type oxygen absorption apparatus. See Dornte "Oxidation of White Oils," Industrial and Engineering Chemistry, vol. 28, pp. 26-30, 1936. Normally, the conditions are one atmosphere of pure oxygen at 340° F. (171° C.). The results are reported in hours to absorb 1000 mL (1 L) of $O_2$ by 100 grams of oil.

With respect to describing molecules and/or molecular fragments herein, "$R_x$," where "x" is merely an identifier, refers to a hydrocarbon group, wherein the molecules and/or molecular fragments can be linear and/or branched, and unless stated otherwise, groups identified by different "x" identifiers can be the same or different.

As defined herein, "carbon number," as it relates to a hydrocarbon molecule or fragment (e.g., an alkyl group), is an integer denoting the total number of carbon atoms in the fragment or molecule. Carbon number with such a fragment or molecule can also be denoted as "$C_y$," where "y" is the total number of carbon atoms within that particular fragment or molecule.

"Triglyceride," as defined herein, refers to class of molecules having the following molecular structure:

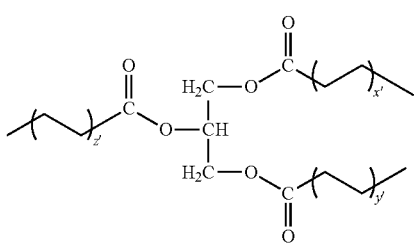

where x', y', and z' can be the same or different, and wherein one or more of the branches defined by x', y', and z' can have unsaturated regions.

A "carboxylic acid" or "fatty acid," as defined herein, is a class of organic acids having the general formula:

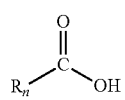

where "$R_n$" is generally a saturated (alkyl)hydrocarbon chain or a mono- or polyunsaturated (alkenyl)hydrocarbon chain.

"Lipids," as defined herein, broadly refers to the class of molecules comprising fatty acids, and tri-, di-, and mono-glycerides.

"Hydrolysis" of triglycerides yields free fatty acids and glycerol, such fatty acid species also commonly referred to as carboxylic acids (see above).

"Transesterification," or simply "esterification," refers to the reaction between a fatty acid or ester (e.g., a triglyceride) and an alcohol to yield an ester species.

The term, "mono-unsaturated free lipid species," as defined herein, refers to mono-unsaturated fatty acids and/or mono-unsaturated fatty esters—typically such species being derived from triglyceride species via hydrolysis and/or transesterification, wherein at least some of the triglyceride species comprise at least one mono-unsaturated fatty chain, i.e., a hydrocarbon chain having a single carbon-carbon double bond.

The prefix "bio," as used herein, refers to an association with a renewable resource of biological origin, such as resource generally being exclusive of fossil fuels.

The term "bio-derived," as defined herein, refers to derivation from a renewable biological resource, organism, or entity; and it generally precludes derivation from fossil fuels, the latter not being deemed "renewable."

The terms "biomass precursor species" and "biomass precursor material," as used (interchangeably) herein, refer to biomass or biomass derivatives from which bio-derived reagents and/or products can be synthesized or otherwise manufactured.

"Fischer-Tropsch products," as defined herein, refer to molecular species derived from a catalytically-driven reaction between CO and $H_2$ (i.e., "syngas"). See, e.g., Dry, "The Fischer-Tropsch process: 1950-2000," vol. 71(3-4), pp. 227-241, 2002; Schulz, "Short history and present trends of Fischer-Tropsch synthesis," Applied Catalysis A, vol. 186, pp. 3-12, 1999.

"Isomeric mixtures," as defined herein, refers to a mixture of quantities of at least two different molecular species having the same chemical formula and molecular weight, but having a different structural arrangements—in terms of the atoms making up the at least two different molecular species.

3. Diester Lubricant Compositions

In some embodiments, the present invention is generally directed to diester-based lubricant compositions comprising a quantity of at least one isomeric mixture of diester species having the following chemical structures:

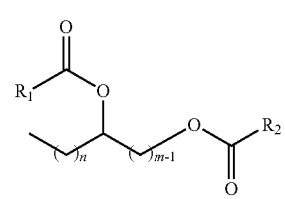
(1a)

+

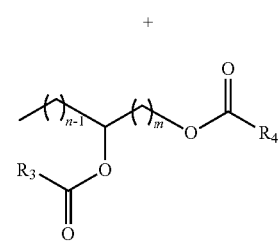
(1b)

wherein $R_1$, $R_2$, $R_3$, and $R_4$ are the same or independently selected from $C_1$ to $C_{20}$ hydrocarbon groups, and wherein n and m are the same or independently selected from the group of integers 2 to 20.

In some such above-described compositional embodiments, the kinematic viscosity of the resulting composition at a temperature of 100° C. is at least 3 mm²/s Additionally or alternatively, in some such compositional embodiments, said composition has a pour point of less than −20° C. Typically, in such embodiments, diester structures are selected, and additional components present (if at all), so as to provide for a lubricant composition having such aforementioned properties.

In some such above-described compositional embodiments, $R_1$ and $R_2$ are independently selected to have a carbon number from at least about 1 to at most about 15. Additionally or alternatively, in some such embodiments, $R_3$ and $R_4$ are independently selected to have a carbon number from at least about 1 to at most about 15. In some or other such embodiments, n is an integer from 5 to 10. In some or still other such embodiments, m is an integer from 5 to 10.

In some such above-described compositional embodiments, the isomeric diester species, of which the at least one isomeric mixture is comprised, each having a molecular mass that is from at least about 400 atomic mass units (a.m.u.) to at most about 1100 a.m.u., and more typically between 450 a.m.u. and 1000 a.m.u.

Referring to the structures in FIG. 1, in some embodiments, the at least one isomeric mixture of diester species is selected from the group of isomeric diester pairs consisting of octadecane-1,9-diyl dihexanoate (2a) and octadecane-1,10-diyl dihexanoate (2b); octadecane-1,9-diyl bis(decanoate) (3a) and octadecane-1,10-diyl bis(decanoate) (3b); octadecane-1,9-diyl dioctanoate (4a) and octadecane-1,10-diyl dioctanoate (4b); ocatadecane-1,9-diyl didodecanoate (5a) and ocatadecane-1,10-diyl didodecanoate (5b); and mixtures thereof.

Such above-described compositions are not limited to a single isomeric diester pair. In some such above-described compositional embodiments, such lubricant compositions comprise at least two (i.e., two or more) different isomeric mixtures of diester species. As an example, in some embodiments, a particular lubricant composition may comprise quantities of both diester mixture 4a/4b and 5a/5b. In such embodiments, the relative amount of one isomeric mixture of diester species can vary considerably from that of another isomeric mixture of diester species within a given lubricant composition.

In some such above-described compositional embodiments, such compositions are not limited (at least in terms of their ester-component) to diesters in the form of isomeric mixtures of such species. In some such embodiments, such lubricant compositions additionally comprise one or more ester species selected from the group consisting of monoesters, diesters, triesters, and combinations thereof. Types of such additional diester species include, but are not limited to, vicinal diesters such as those described in commonly-assigned U.S. patent application Ser. Nos. 11/673,879 (Miller et al.), filed Feb. 12, 2007 and published as United States Patent Publication No. US 20080194444 on Aug. 14, 2008; and Ser. No. 12/023,695 (Miller et al.), filed Jan. 31, 2008. Types of such triester species include, but are not limited to, those described in commonly-assigned U.S. Pat. No. 7,544,645, issued on Jun. 9, 2009.

In some such above-described compositional embodiments, such lubricant compositions comprise, individual diester isomers 1a and 1b, of which the isomeric mixture of diester species is comprised, differ in relative amount by not more than 5 percent. In some or other such embodiments, 1a and 1b differ in relative amount by not more than 3 percent. In some or still other such embodiments, 1a and 1b differ in relative amount by not more than 1 percent.

In some particular compositional embodiments, at least one of the at least one isomeric diester mixtures take the form of 6a and 6b below, wherein $R_1$, $R_2$, $R_3$, and $R_4$ are selected as described above for 1a and 1b.

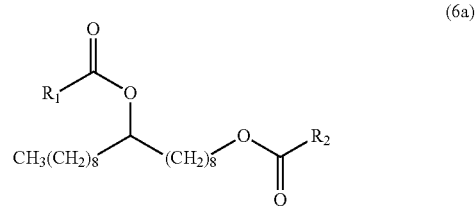

(6a)

+

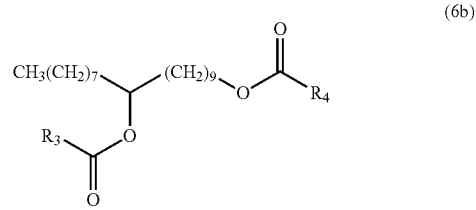

(6b)

It is worth noting that in many applications, the above-described diesters and their compositions are not used as lubricants by themselves, but are used as components and/or blending stocks for more complex lubricant compositions or mixtures. Accordingly, in some such embodiments, the above-described compositions further comprise a base oil selected from the group consisting of Group I oils, Group II oils, Group III oils, and combinations thereof (vide supra). As such, esters with higher pour points may also be used as blending stocks with other lubricant oils since they are very soluble in hydrocarbons and hydrocarbon-based oils.

4. Methods of Making Diester Lubricants

As mentioned above, the present invention is additionally directed to methods of making the above-described (Section 3) lubricant compositions and/or the diester-based compositions contained therein.

Figure 2:
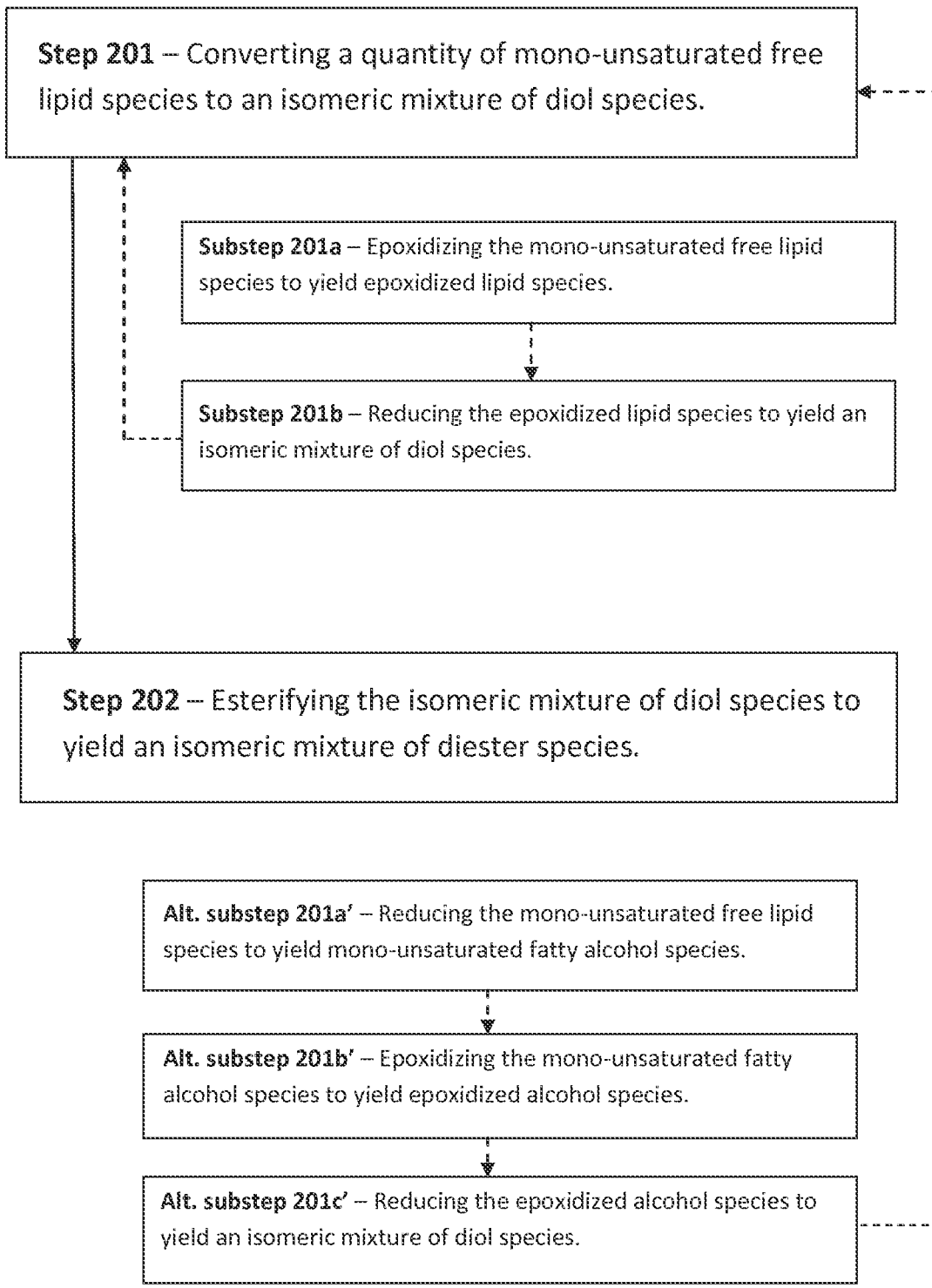
FIG. 2 is a flow diagram describing how isomeric mixtures of diester species are prepared, in accordance with some embodiments of the present invention.

Referring to the flow diagram shown in FIG. 2, in some embodiments, processes/methods for making at least the isomeric diester mixtures of the above-mentioned diester-based compositions comprise the following steps: (Step 201) converting a quantity of mono-unsaturated free lipid species, having a carbon number of from 10 to 22, to an isomeric mixture of diol species having the same carbon number as the free lipid species from which they were derived, wherein said converting proceeds via an epoxide intermediate species; and (Step 202) esterifying the isomeric mixture of diol species with an esterifying species to form an isomeric mixture of diester species, wherein the isomeric mixture of diester species comprises the following isomerically-related structures:

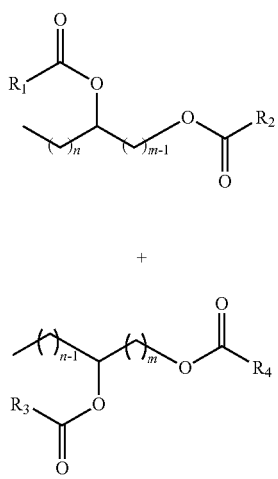

wherein $R_1$, $R_2$, $R_3$, and $R_4$ are the same or independently selected from $C_2$ to $C_{20}$ hydrocarbon groups, and wherein n and m are the same or independently selected from the group of integers 2 to 20.

Referring again to FIG. 2, in some such above-described method embodiments, the step of converting comprises the following sub-steps: (Substep 201a) epoxidizing the quantity of mono-unsaturated free lipid species to yield a quantity of epoxidized lipid species; and (Substep 201b) reducing the epoxidized lipid species to yield an isomeric mixture of diol species.

In some such above-described method embodiments, the substep of epoxidizing (Substep 201a) utilizes a reagent (i.e., an epoxidizing agent/species) selected from one or more species such as, but not limited to, peroxides and peroxy acids. Regarding the above-mentioned substep of epoxidizing, in some embodiments, the above-described mono-unsaturated free lipid species (e.g., oleic acid) can be reacted with a peroxide (e.g., $H_2O_2$) or a peroxy acid (e.g., peroxyacetic acid) to generate an epoxy-fatty acid species. See, e.g., Swern et al., "Epoxidation of Oleic Acid, Methyl Oleate and Oleyl Alcohol with Perbenzoic Acid," J. Am. Chem. Soc., vol. 66(11), pp. 1925-1927, 1944. Another exemplary peroxy acid for use in Substep 201a is meta-chloro-peroxybenzoic acid (mCPBA).

In some such above-described method embodiments, the substep of reducing utilizes a metal-hydride reducing agent. Regarding the above-described substep of reducing (Substep 201b), in some embodiments, lithium aluminum hydride (LiAlH$_4$) is used as a reducing agent to effect such reduction. In some or other embodiments, particularly for industrial-scale processes, catalytic hydrogenation may be employed using, for example, copper- or zinc-based catalysts. See, e.g., U.S. Pat. No. 4,880,937; Scrimgeour, "Chemistry of Fatty Acids," in *Bailey's Industrial Oil and Fat Products, 6$^{th}$ Edition, Vol. 1*, pp. 1-43, F. Shahidi (Ed.), J. Wiley & Sons, New York, 2005.

In some such above-described method embodiments, the step of esterifying the isomeric mixture of diol species with an esterifying species first involves conversion of one or more fatty acid species to one or more corresponding esterification species selected from the group consisting of acyl halide species, it/they selected from the group consisting of acyl chlorides, acyl bromides, acyl iodides, and combinations thereof; and acyl anhydride species. The esterification species can react with the —OH groups of the diols to form diester species. In some such above-described method embodiments, the step of esterifying the isomeric mixture of diol species with an esterifying species involves a catalyst selected from the group consisting of an acid catalyst and a base catalyst.

Regarding the step of esterifying the isomeric mixture of diol species to form an isomeric diester mixture, in some embodiments an acid can be used to catalyze the reaction between the —OH groups of the diol and the carboxylic acid(s). Suitable acids include, but are not limited to, sulfuric acid (Munch-Peterson, Org. Synth., Coll. Vol. 5, p. 762, 1973), sulfonic acid (Allen and Sprangler, Org. Synth., Coll. Vol. 3, p. 203, 1955), hydrochloric acid (Eliel et al., Org. Synth., Coll. Vol. 4, p. 169, 1963), and phosphoric acid (among others). In some such embodiments, the carboxylic acid used in this step is first converted to an acyl chloride (or another acyl halide) via, e.g., thionyl chloride or PCl$_3$. Alternatively, an acyl chloride (or other acyl halide) could be employed directly. Where an acyl chloride is used, an acid catalyst is not needed and a base such as pyridine, 4-dimethylaminopyridine (DMAP) or triethylamine (TEA) is typically added to react with an HCl produced. When pyridine or DMAP is used, it is believed that these amines also act as a catalyst by forming a more reactive acylating intermediate. Accordingly, such esterification steps can also be base-catalyzed. See, e.g., Fersht et al., "Acetylpyridinium ion intermediate in pyridine-catalyzed hydrolysis and acyl transfer reactions of acetic anhydride. Observation, kinetics, structure-reactivity correlations, and effects of concentrated salt solutions," J. Am. Chem. Soc., vol. 92(18), pp. 5432-5442, 1970; and Hofle et al., "4-Dialkylaminopyradines as Highly Active Acylation Catalysts," Angew. Chem. Int. Ed. Engl., vol. 17, pp. 569-583, 1978. Additionally or alternatively, the carboxylic acid could be converted into an acyl anhydride and/or such species could be employed directly.

In some such above-described method embodiments, there further comprises a step of blending the isomeric mixture of diester species with one or more other ester species selected from the group consisting of triesters, diesters, monoesters, and combinations thereof. Such one or more other ester species, particularly in the case of other diester species, need not be provided as isomeric mixtures. Additionally or alternatively, in some such above-described method embodiments, there further comprises a step of blending the isomeric mixture of diester species with a base oil selected from the group consisting of Group I oils, Group II oils, Group III oils, and combinations thereof.

In some such above-described method embodiments, the isomeric mixture of diester species is entirely bio-derived, meaning that the synthesis of said species uses (exclusive of solvents and catalysts) only bio-derived reagents. In some or other embodiments, such bio-derived isomeric mixtures of diester species are subsequently mixed or blended with other components and/or mixtures not entirely of bio-derivation to yield lubricant compositions that are only partially bio-derived.

Generally, lubricant compositions made by such methods and comprising such diester species have a viscosity of 3 mm$^2$/s (centistokes) or more at a temperature of 100° C. and they typically have a pour point of less than −20° C., and selection of reagents and/or mixture components is typically made with this objective.

In some embodiments, such methods produce compositions (vide supra) comprising at least one isomeric mixture of diester species selected from among the following isomeric diester pairs: octadecane-1,9-diyl dihexanoate (2a) and octadecane-1,10-diyl dihexanoate (2b); octadecane-1,9-diyl bis (decanoate) (3a) and octadecane-1,10-diyl bis(decanoate) (3b); octadecane-1,9-diyl dioctanoate (4a) and octadecane-1, 10-diyl dioctanoate (4b); ocatadecane-1,9-diyl didodecanoate (5a) and ocatadecane-1,10-diyl didodecanoate (5b); and mixtures thereof. Such isomeric mixtures can be prepared by using oleic acid, or, e.g., methyl oleate, as the initial mono-unsaturated free lipid species.

In some such above-described embodiments, the lubricant compositions produced by such methods comprise individual diester isomers 1a and 1b that differ in relative amount by not more than 5 percent. In some or other such embodiments, 1a and 1b differ in relative amount by not more than 3 percent. In some or still other such embodiments, 1a and 1b differ in relative amount by not more than 1 percent. While not intending to be bound by theory, deviation from equivalent isomer amounts in a given isomeric mixture of diester species can be attributed to one or more scenarios including, but not limited to, rearrangements, solvent effects on transition state, and statistical factors.

In some such above-described method embodiments, the mono-unsaturated free lipid species can be a bio-derived fatty acid (or ester) formed by hydrolysis (or esterification) of one or more triglyceride-containing vegetable oils such as, but not limited to, palm oil, sunflower oil, rapeseed oil, olive oil, linseed oil, and the like. Other sources of triglycerides, for which hydrolysis can yield unsaturated fatty acids, include, but are not limited to, algae, animal tallow, and zooplankton. See, e.g., Bajpai et al., "Biodiesel: Source, Production, Composition, Properties and Its Benefits," J. Oleo Sci., vol. 55(10), pp. 487-502, 2006 (general review); Sargent et al., "Biosynthesis of Lipids in Zooplankton from Saanich Inlet, British Columbia, Canada," Marine Biology, vol. 31, pp. 15-23, 1975 (zooplankton as a source of lipids).

In some embodiments, wherein the above-mentioned hydrolyzed triglyceride sources contain mixtures of saturated fatty acids, mono-unsaturated fatty acids, and poly-unsaturated fatty acids, one or more techniques may be employed to isolate, concentrate, or otherwise separate the mono-unsaturated fatty acids from the other fatty acids in the mixture. See, e.g., commonly-assigned United States Patent Application by Miller entitled, "Isolation and Subsequent Utilization of Saturated Fatty Acids and α-Olefins in the Production of Ester-Based Biolubricants," Ser. No. 12/122,894, filed May 19, 2008.

In some embodiments, partial hydrogenation of polyunsaturated fatty acids can yield mono-unsaturated fatty acids for use in methods of the present invention. Post hydrogenation, such mono-unsaturated fatty acids may be subjected to one or more of the above-mentioned separation/isolation techniques. See, e.g., Falk et al., "The Effect of Fatty Acid Composition on Biodiesel Oxidative Stability," Eur. Journal of Lipid Sci. & Technol., vol. 106(12), pp. 837-843, 2004.

Figure 3:
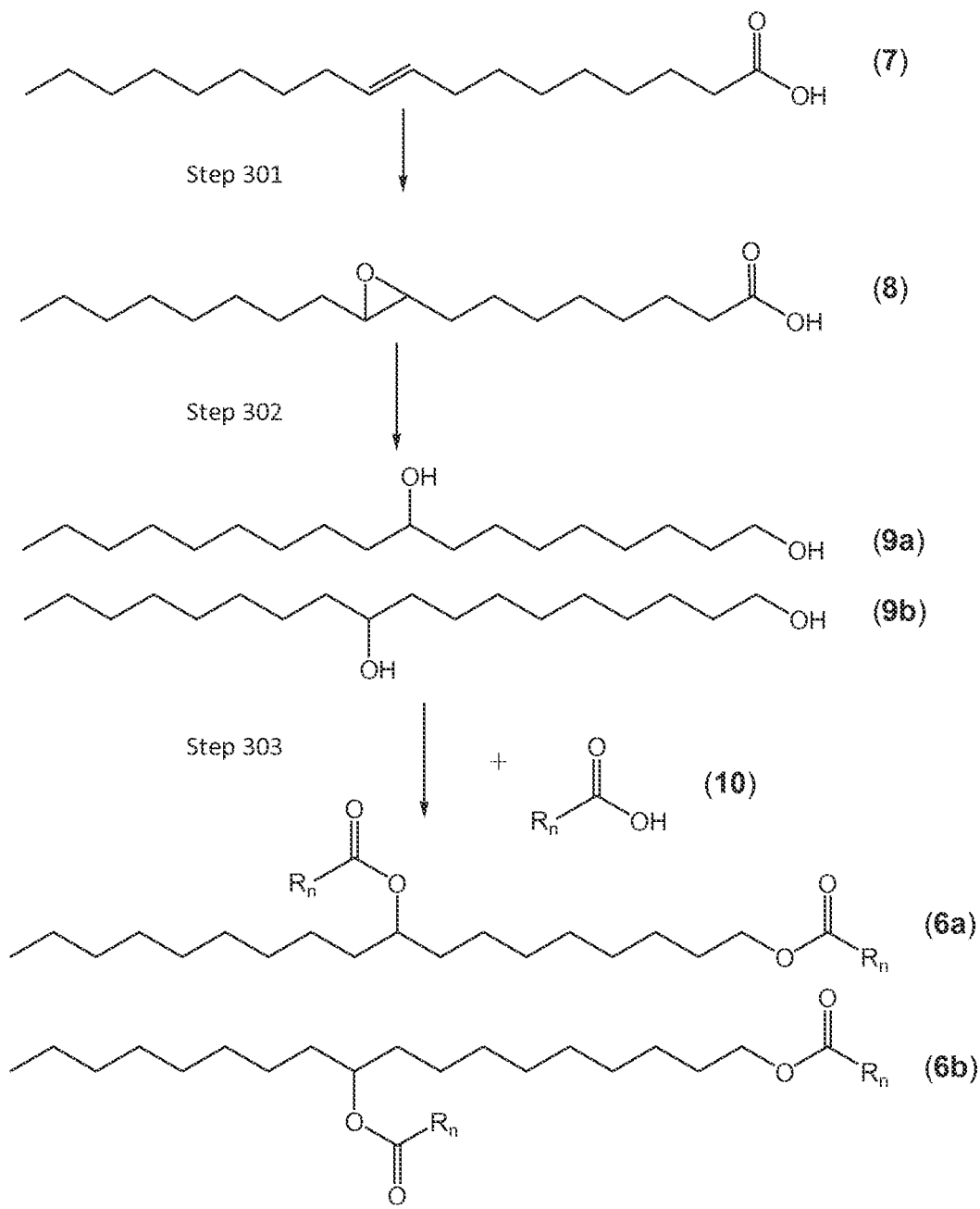
FIG. 3 (Scheme 1) is a chemical flow diagram illustrating some representative methods of making (synthesizing) a diester-based lubricant composition (or at least a diester component thereof), in accordance with some embodiments of the present invention, wherein oleic acid is used as a representative mono-unsaturated fatty acid.

Referring to Scheme 1 (FIG. 3), said scheme being illustrative and representative of some such above-described embodiments, oleic acid (7) is epoxidized with an epoxidizing agent (e.g., a peroxy acid) to yield epoxy-lipid (epoxy-fatty acid) species 8 (Step 301). With continued reference to Scheme 1, epoxy-lipid species 8 is reduced, using a reducing agent (e.g., LiAlH$_4$), to an isomeric mixture of diol species (9a/9b) (Step 302). Lastly, the mixture of diol species 9a and 9b is esterified with esterification agent 10 to yield isomeric mixture of diester species 6a/6b (Step 303).

Regardless of the source of the mono-unsaturated free lipid species (vide supra), in some embodiments, the carboxylic acids (or their acyl derivatives) used in the above-described methods are derived from biomass. In some such embodiments, this involves the extraction of some oil (e.g., triglyceride) component from the biomass and hydrolysis of the triglycerides of which the oil component is comprised so as to form free carboxylic acids. Other sources of such carboxylic acids include, but are not limited to, those derived (directly or indirectly)

5. Variations

Referring again to FIG. 2, in some embodiments, variations on the above-described method embodiments are found wherein the step of converting comprises the following alternate (variational) sub-steps: (Alt. Substep 201a') reducing the quantity of mono-unsaturated free lipid species to yield a quantity of mono-unsaturated fatty alcohol species; (Alt. Substep 201b') epoxidizing the quantity of mono-unsaturated fatty alcohol species to yield a quantity of epoxidized alcohol species; and (Alt. Substep 201c') reducing the epoxidized alcohol species to yield an isomeric mixture of diol species. In some such variational embodiments, the variational substeps of reducing the quantity of mono-unsaturated free lipid species and reducing the epoxidized alcohol species utilize one or more metal-hydride reducing agents. In some or other such variational embodiments, the variational substep of epoxidizing the quantity of mono-unsaturated fatty alcohol species utilizes an oxidizing agent selected from the group consisting of peroxides and peroxy acids. Generally, all other aspects of such alternate method embodiments are consistent with the corresponding aspects of the method embodiments described in the preceding section (Section 4).

Figure 4:
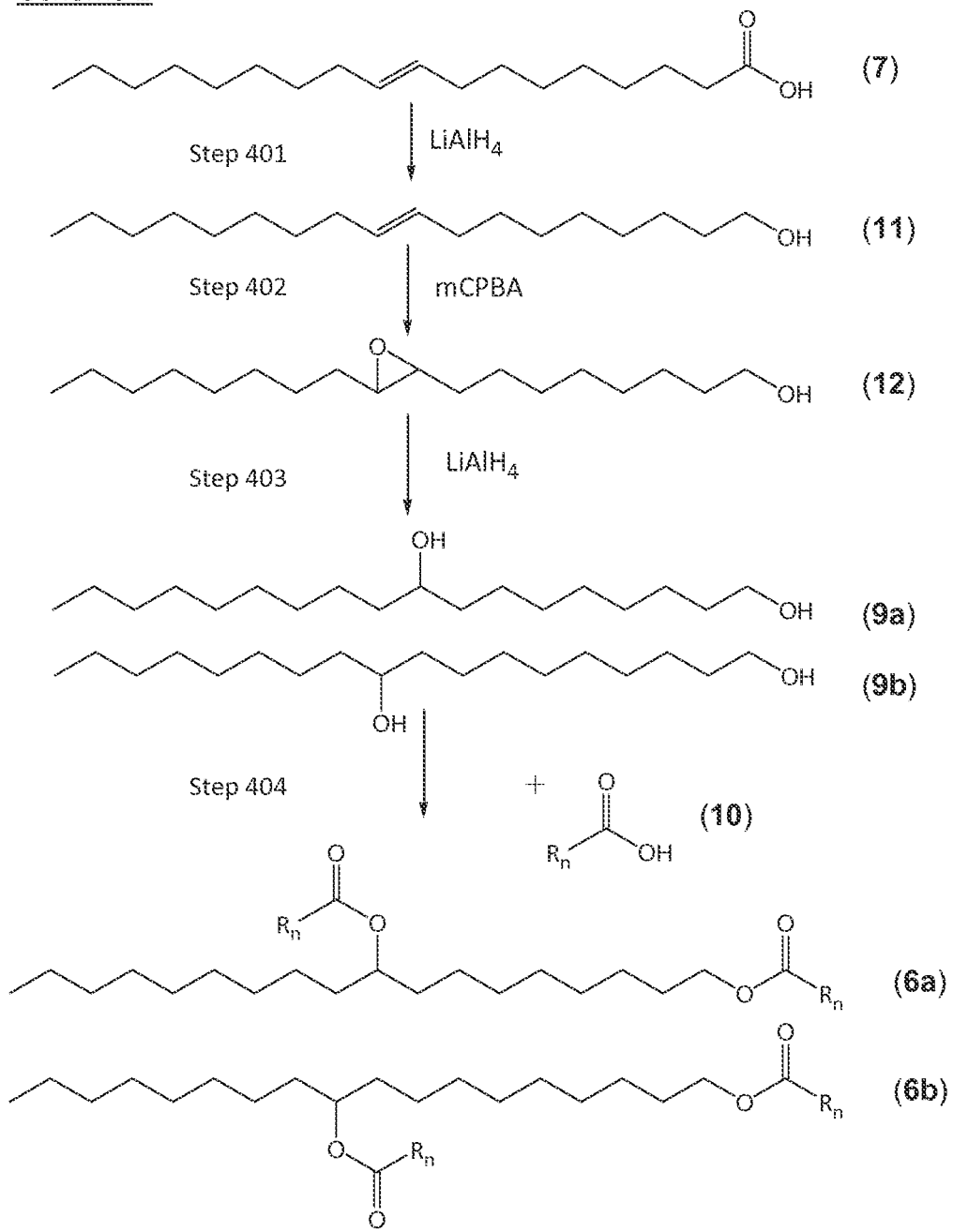
FIG. 4 (Scheme 2) is a chemical flow diagram illustrating one or more alternate methods of making a diester-based lubricant composition (or at least a diester component thereof), in accordance with some embodiments of the present invention, wherein oleic acid is used as a representative mono-unsaturated fatty acid.

Referring to Scheme 2 (FIG. 4), said scheme being illustrative and representative of some such above-described alternate method embodiments, embodiments, oleic acid (7) is reduced with a representative reducing agent/species (LiAlH$_4$) to yield oleoyl alcohol 11 (Step 401). Oleoyl alcohol 11 is then epoxidized with an epoxidizing agent (mCPBA) to yield epoxy-alcohol species 12 (Step 402) and the epoxy-alcohol species 12 is reduced with a reducing species to yield an isomeric mixture of diol species 9a and 9b (Step 403). Lastly, the isomeric mixture of diester species 9a and 9b is reacted with esterification agent 10 to yield an isomeric mixture of diester species 6a and 6b (Step 404).

Additional and/or alternative variations on the above-described methods include, but are not limited to, generating (and utilizing) compositional ranges of isomeric diester pairs by blending and/or by compositional variation in the reagents used during the synthesis of the diester species described herein. Compositions produced by such method variations will, naturally, be variations themselves. Generally, all such variations fall within the scope of the compositions and methods described herein.

In some additional or alternative variational embodiments, molecular averaging can be employed to generate greater molecular homogeneity in the resulting compositions (at least in terms of the diester species contained therein) by furthering the homogeneity of the quantity of mono-unsaturated free lipid species—if not already in a fairly homogeneous state. Such molecular averaging techniques involve olefin metathesis and are generally described in the following commonly-assigned United States Patents: U.S. Pat. No. 6,566,568 by Chen, issued May 20, 2003; U.S. Pat. No. 6,369,286 by O'Rear, issued Apr. 9, 2002; and U.S. Pat. No. 6,562,230 by O'Rear et al., issued May 13, 2003.

In some additional or alternative variational embodiments, at least a portion of the mono-unsaturated free lipid species are initially subjected to skeletal isomerization techniques such that the resulting lubricant compositions additionally comprise more highly branched diester species. See, e.g., U.S. Pat. No. 6,831,184 (Zhang et al.), issued Dec. 14, 2004, for a method of catalytically-isomerizing fatty acids. Additionally or alternatively, in some such embodiments, such more highly branched diester species can be added so as to provide for lubricant compositions comprising additional diester species (vide supra).

6. EXAMPLES

The following examples are provided to demonstrate particular embodiments of the present invention. It should be appreciated by those of skill in the art that the methods disclosed in the examples which follow merely represent exemplary embodiments of the present invention. However, those of skill in the art should, in light of the present disclosure, appreciate that many changes can be made in the specific embodiments described and still obtain a like or similar result without departing from the spirit and scope of the present invention.

Figure 5:
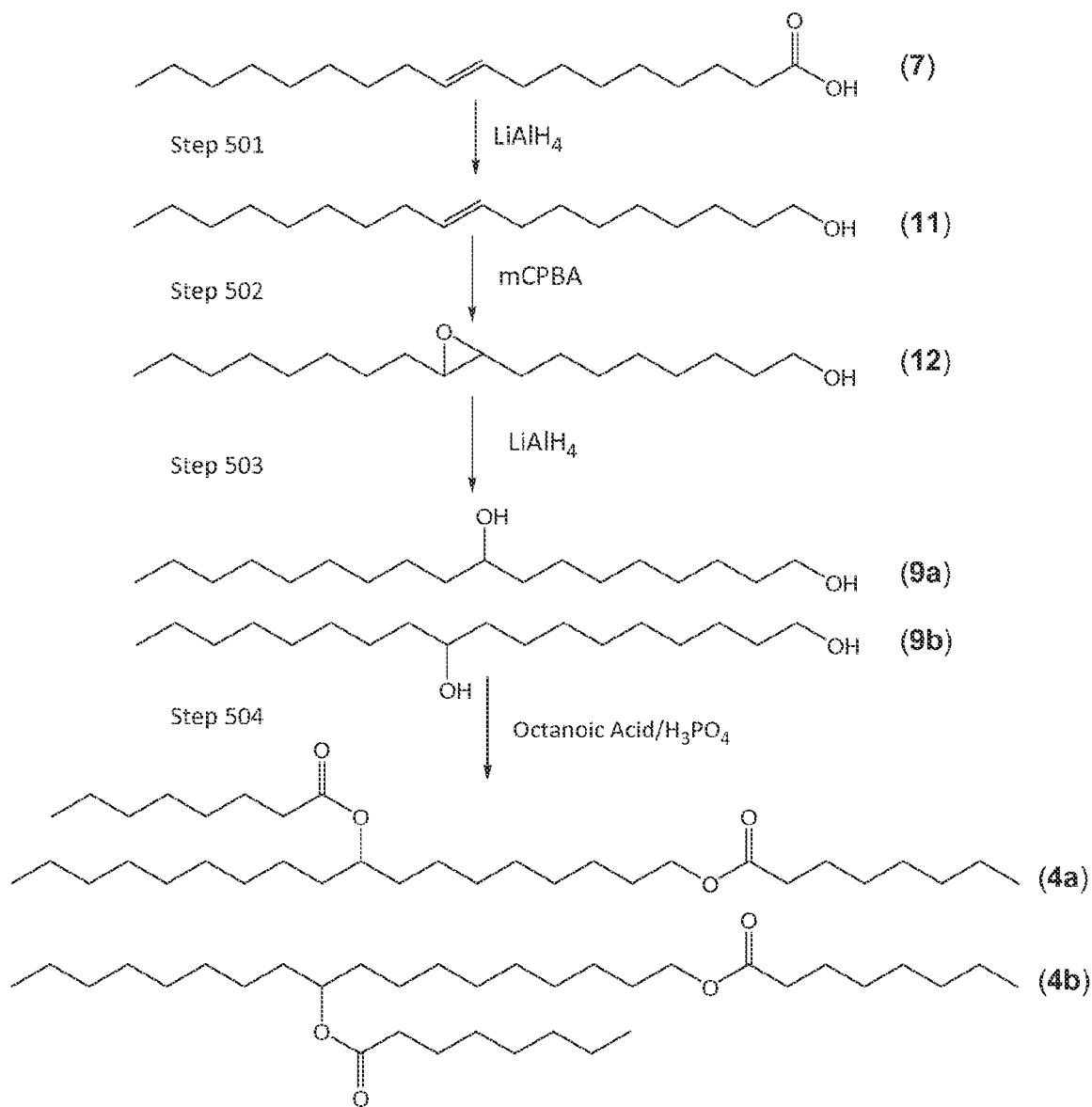
FIG. 5 (Scheme 3) is a chemical flow diagram illustrating methods of making a diester-based lubricant composition (or at least a diester component thereof) from oleic acid, in accordance with some embodiments of the present invention, and as illustrated in Examples 1-4.

As an exemplary synthetic procedure for making at least an ester component of one or more of the diester-based lubricant compositions described above, the synthesis of isomeric diester mixture 4a and 4b (Scheme 3, FIG. 5) is described in Examples 1-4 which follow. Note that this procedure is representative for making isomeric diester mixtures from mono-unsaturated free lipid species (e.g., oleic acid), in accordance with some embodiments of the present invention.

Example 1

This Example serves to illustrate synthesis of mono-unsaturated fatty alcohol 11, in accordance with some embodiments of the present invention, and en route to the formation of isomeric diester mixture 4a/4b. Referring to Scheme 3 (FIG. 5) oleic acid 7 was reduced to the corresponding oleyl alcohol 11 (Step 501) as follows.

To an ice-cold (i.e., in an ice bath) suspension of 43 grams (1.13 mol) of lithium aluminum hydride ($LiAlH_4$) in tetrahydrofuran (THF) in a 3-neck 3-liter reaction flask fitted with an overhead stirrer and a reflux condenser, 150 grams (0.53 mol) of oleic acid 7 was added drop-wise over a period of 45 minutes via an addition funnel. The resulting reaction mixture was allowed to warm gradually to room temperature, after which the ice bath was replaced with a heating mantle and the reaction mixture was refluxed for 4 hours. After refluxing, the reaction mixture was allowed to cool to room temperature and left to stir overnight. The reaction progress was monitored by infrared (IR) and nuclear magnetic resonance (NMR) spectroscopies for the disappearance of the acid carbonyl group. The reaction was worked up by dilution with 500 mL of diethyl ether followed by slow addition (drop-wise) of 350 mL of 15 wt % NaOH aqueous solution at 0° C. under vigorous stirring, followed by the addition of 50 mL of water. The resulting two-layer solution, a white solid precipitate and clear organic layer, was filtered to remove the solids (unwanted inorganic salts). The organic layer was dried over anhydrous $MgSO_4$, filtered, and concentrated on a rotary evaporator (rotovap) to give oleyl alcohol 11 as colorless oil. The reaction afforded 133 grams (93% yield) of the desired oleyl alcohol. The product was authenticated with NMR and IR spectroscopic analyses, as well as gas-chromatographic/mass-spectrometric (GC/MS) analysis.

Example 2

This Example serves to illustrate the synthesis of epoxy-alcohol species 12 (oleyl epoxide), en route to the synthesis of isomeric diester mixture 4a/4b and in accordance with some embodiments of the present invention. Referring again to Scheme 3 (FIG. 5), epoxy-alcohol species 12 was prepared from oleyl alcohol 11 (Step 502) according to the following procedure.

To an ice-cold (ice-bath) solution of 52 grams of 75 wt % mCPBA (meta-chloro-peroxybenzoic acid) in 300 mL of methylene chloride ($CH_2Cl_2$) in a 3-neck 1 L reaction flask, 50 grams of oleyl alcohol 11, prepared as described above in Example 1, was added drop-wise over a 45 minute period. The reaction was allowed to slowly warm to room temperature, after which it was left to stir overnight at room temperature. The following day, the reaction mixture (solids+clear liquid) was filtered. The filtrate was rinsed once with 150 mL of 10 wt % $NaSO_3$ aqueous solution, once with 200 mL of saturated $KHCO_3$ solution, and three times with 300 mL of water. The organic layer was dried over $MgSO_4$, filtered, and concentrated on a rotary evaporator to give the product as a waxy, solid material in 93% yield (48 grams) with high purity according to GC/MS analysis. Note that methyl oleate was also epoxidized using the same epoxidation procedure to give the corresponding epoxy methyl oleate.

Example 3

With continued reference to Scheme 3 (FIG. 5), this Example serves to illustrate how the epoxy-alcohol species 12 is converted (reduced) to an isomeric mixture of diol species 9a/9b (Step 503), in accordance with some embodiments of the present invention. Isomeric mixture 9a/9b was prepared according to the procedure that follows.

To an ice-cold suspension of 20 grams of $LiAlH_4$ in 350 mL THF in 3-neck 2 L reaction flask (fitted with a reflux condenser and an overhead stirrer), 46 grams of epoxy alcohol 12 (synthesized as described above in Example 2 and dissolved in 200 mL of THF) were added drop-wise over a 30 minute period. The resulting mixture was left to warm to room temperature and then heated to reflux for few hours. The reaction was then allowed to stir at room temperature overnight. The next day, the reaction was placed in an ice-bath and diluted with 300 mL of ether. The ice-cold reaction mixture was treated by slowly adding 200 mL of 15 wt % NaOH solution followed by 30 mL of water with vigorous stirring. The resulting two phase mixture (liquid layer+white precipitate) was filtered and the filtrate dried over $MgSO_4$, then filtered again and concentrated to give an isomeric mixture of diol species 9a/9b as a white powder in 88% yield (41 grams). The diols 9a and 9b were identified by spectral analysis (IR, NMR and GCMS). Note that epoxy methyl oleate was similarly reduced with lithium aluminum hydride according to the procedure above to give the diols 9a and 9b described above.

Example 4

This Example serves to illustrate the synthesis of isomeric diester mixture 4a/4b, in accordance with some embodiments of the present invention. Referring once again to Scheme 3 (FIG. 5), the synthesis of octadecane-1,9-diyl dioctanoate/octadecane-1,10-diyl dioctanoate (4a/4b) was carried out via the esterification of diol mixture 9a/9b (Step 504) as follows.

In a 250 mL 3-neck reaction flask fitted with an overhead stirrer, nitrogen bubbler, and Dean-Stark trap, 85.8 grams (0.3 mol) of the isomeric mixture of diol species 9a/9b (prepared as described above in Example 3) was mixed with 129.6 grams (0.9 mol) of octanoic acid and 2.76 grams of 85 wt % $H_3PO_4$ at room temperature. The resultant mixture was stirred and heated to 160° C. with nitrogen bubbling through the mixture. After 8 hours, the reaction was complete and was cooled to room temperature. The mixture was stirred with sodium bicarbonate (3 grams) for 30 minutes and then filtered. The mixture was distilled under a vacuum of 10 mm Hg (Torr) to remove excess octanoic acid. The desired diester product 4a/4b was obtained in 75% yield. The lubrication and physical properties of diester product 4a/4b are shown in Table 1 (FIG. 6).

7. Summary

In summary, the present invention provides for diester-based lubricant compositions comprising isomeric mixtures of diester species. The present invention also provides for methods (processes) of making these and other similar lubricant compositions. In some embodiments, the methods for making such diester-based lubricants utilize a biomass-derived precursor comprising mono-unsaturated fatty acids and/or esters, wherein such mono-unsaturated fatty acids/esters are converted to one or more isomeric diol species en route to the synthesis of diester-based lubricant compositions. Subsequent steps on the path to such synthesis may employ carboxylic acids and/or acyl halides/anhydrides derived from biomass and/or Fischer-Tropsch synthesis. In some such embodiments, at least the isomeric mixtures of diester species, of which the diester-based lubricant compositions are comprised, are entirely bio-derived.

All patents and publications referenced herein are hereby incorporated by reference to the extent not inconsistent herewith. It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention may be practiced otherwise than as specifically described without actually departing from the spirit and scope of the present invention as defined by the appended claims.

What is claimed is:

1. A lubricant composition comprising at least one isomeric mixture of diester species comprising the following isomerically-related diester structures:

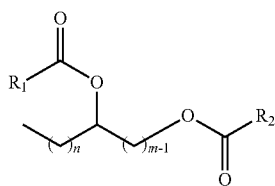

(1a)

+

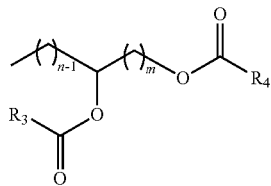

(1b)

wherein $R_1$, $R_2$, $R_3$, and R4 are the same or independently selected from $C_1$ to $C_{20}$ hydrocarbon groups, and wherein n is independently selected from the group of integers 2 to 20, and m=2, the structure represented by (1a) being a vicinal ester.

2. The lubricant composition of claim 1 wherein the kinematic viscosity of the lubricant composition at temperature of 100° C. is at least 3 mm²/s.

3. The lubricant composition of Claim1, said composition having a pour point of less than −20° C.

4. The lubricant composition of claim 1, wherein $R_1$ is selected to have a carbon number from at least about 1 to at most about 15.

5. The lubricant composition of claim 1, wherein $R_2$ is selected to have a carbon number from at least about 1 to at most about 15.

6. The lubricant composition of claim 1, comprising at least two different isomeric mixtures of diester species.

7. The lubricant composition of claim 1, wherein n is selected from the group of integers 5 to 10.

8. The lubricant composition of claim 1, wherein said composition comprises quantities of at least two different isomeric mixtures of diester species.

9. The lubricant composition of claim 1, wherein the isomeric diester species, of which the at least one isomeric mixture is comprised, have a molecular mass that is from at least about 400 a.m.u. to at most about 1100 a.m.u.

10. The lubricant composition of claim 1, further comprising a base oil selected from the group consisting of Group I oils, Group II oils, Group III oils, and combinations thereof.

11. The lubricant composition of claim 1, further comprising one or more ester species selected from the group consisting of monoesters, diesters, triesters, and combinations thereof.

12. The lubricant composition of claim 1, wherein individual diester isomers 1a and 1b, of which the isomeric mixture of diester species is comprised, differ in relative amount by not more than 5 percent.

* * * * *